United States Patent [19]
Kaneko et al.

[11] Patent Number: 5,374,739
[45] Date of Patent: Dec. 20, 1994

[54] MITOMYCIN ANALOGS

[75] Inventors: Takushi Kaneko, Guilford; Henry S. L. Wong, Durham; Terrence W. Doyle, Killingworth, all of Conn.

[73] Assignee: Bristol-Myers Squibb Company, New York, N.Y.

[21] Appl. No.: 68,833

[22] Filed: May 28, 1993

Related U.S. Application Data

[60] Continuation of Ser. No. 752,929, Aug. 30, 1991, abandoned, which is a continuation of Ser. No. 631,177, Dec. 19, 1990, abandoned, which is a continuation of Ser. No. 520,996, May 9, 1990, abandoned, which is a continuation of Ser. No. 413,418, Sep. 27, 1989, abandoned, which is a division of Ser. No. 61,839, Jun. 12, 1987, abandoned.

[51] Int. Cl.$^5$ .................... C07D 487/14; A61K 31/40
[52] U.S. Cl. .................................................. 548/422
[58] Field of Search ........................................ 548/422

[56] References Cited

U.S. PATENT DOCUMENTS

| | | | |
|---|---|---|---|
| 3,332,944 | 7/1967 | Cosulich et al. | 260/247.2 |
| 3,420,846 | 1/1967 | Matsui et al. | 260/326.3 |
| 3,450,705 | 6/1969 | Matsui et al. | 260/326.3 |
| 3,514,452 | 5/1970 | Matsui et al. | 260/240 |
| 4,231,936 | 11/1980 | Nakano et al. | 260/326.24 |
| 4,268,676 | 5/1981 | Remers | 548/187 |
| 4,460,599 | 7/1984 | Remers | 424/274 |
| 4,487,769 | 12/1984 | Vyas et al. | 424/246 |
| 4,567,256 | 1/1986 | Vyas et al. | 544/58.2 |
| 4,579,737 | 4/1986 | Vyas et al. | 514/236 |

FOREIGN PATENT DOCUMENTS 2165249A 4/1986 United Kingdom.

OTHER PUBLICATIONS

Chemical Abstracts vol. 116:75778 (1992).
Chemical Abstracts vol. 113:58753 (1990).
Chemical Abstracts vol. 111:214327 (1989).
Chemical Abstracts vol. 106:32718 (1987).
Matsui, et al., *Antibiotics,* XXI, 189–198 (1968).
Konishita et al., *J. Med. Chem.,* 14 103–109 (1971).
Iyengar et al., *J. Med. Chem.,* 24 975–981 (1981).
Iyengar, Sami, Remers and Bradner, Abstracts of Papers, 183rd Annual Mtg. of the American Chem. Soc., Las Vegas, Nev., Mar. 1982, Abstract No. MEDI 72.
Iyengar et al., *J. Med. Chem.,* 26, 16–20 (1983).
Iyengar et al., *J. Med. Chem.,* 26, 1453–1457 (1983).
*Activity of C-7 Substituted Cyclic Acetal Derivatives of Mitomycin C and Porfiromycin Against Hypoxic and Oxygenated EMT6 Carcinoma Cells In Vitro and In Vivo;* Rockwell et al; Cancer Communications, vol. 3, No. 6, 1991, pp. 191–198.

*Primary Examiner*—Nicholas S. Rizzo
*Attorney, Agent, or Firm*—Aldo A. Algieri

[57] ABSTRACT

The present invention provides novel mitomycin analogs containing a cyclic acetal or thioacetal group. These compounds are mitomycin C analogs in which the 7-amino group bears a 5-membered heterocyclic substituent. Mitomycin C is an antitumor agent of established utility, and the 7-N-substituted mitosane analogs thereof have similar utility.

3 Claims, No Drawings

MITOMYCIN ANALOGS

This is a continuation of application Ser. No. 07/752,929, filed on Aug. 30, 1991 now abandoned for MITOMYCIN ANALOGS; which is a continuation of application Ser. No. 07/631,177, filed Dec. 19, 1990; now abandoned; which is a continuation of application Ser. No. 07/520,996, filed May 9,1990, now abandoned; which is a continuation of application Ser. No. 07/413,418, filed Sep. 27, 1989, now abandoned; which is a divisional of application Ser. No. 07/061,839, filed Dec. 6, 1987, now abandoned.

BACKGROUND OF THE INVENTION

1. Field of the Invention

The present invention provides novel mitomycin analogs containing a cyclic acetal or thioacetal group and to their use in the treatment of neoplastic disease states in animals. These compounds are mitomycin C analogs in which the 7-amino groups bears a 5-membered heterocyclic substituent. Mitomycin C is an antibiotic of established utility, and the 7-N-substituted mitosane analogs thereof have similar utility.

Nomenclature—The systematic Chemical Abstracts name for mitomycin A based on the recent revision [Shirhata et al., J. Am. Chem. Soc., 105, 7199 (1983)] is:

[1aS-(1a$\beta$,8$\beta$,8a-$a$,8b$\beta$)]-8-[( (aminocarbonyl)oxy)-methyl]-6,8a-dimethoxy-1,1a,2,8,8a,8b-hexahydro-5-methyl-arizino-[2',3',3,4] pyrrolo[1,2-a]indole-4,7-dione according to which the azirinopyrroloindole ring system is numbered as follows:

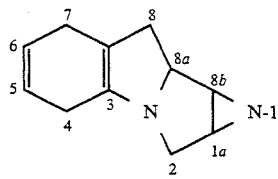

A trivial system of nomenclature which has found wide use in the mitomycin literature identifies the foregoing ring system including several of the characteristic substituents of the mitomycins as mitosane.

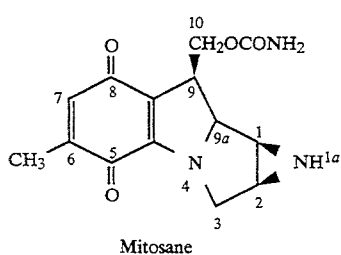

Mitosane

According to this system, mitomycin A is 7,9a-dimethoxymitosane and mitomycin C is 7-amino-9a-methoxy-mitosane. As to the stereochemical configuration of the products of this invention, it is intended when identifying them by the root name "mitosane" or by structural. formula to identify the stereochemical configuration thereof as the same as that of mitomycin C. The structures of Mitomycin A, B, C and of Porfiromycin are set out below:

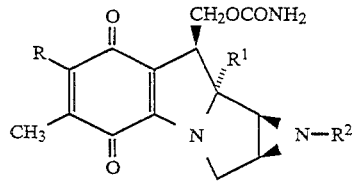

Mitomycin A: R = $R^1$ = $OCH_3$, $R^2$ = H
Mitomycin B: R = $OCH_3$, $R^1$ = OH, $R^2$ = $CH_3$
Mitocycin C: R = $NH_2$, $R^1$ = $OCH_3$, $R^2$ = H
Porfiromycin: R = $NH_2$, $R^1$ = $OCH_3$, $R^2$ = $CH_3$

2. Disclosure Statement

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin R Bristol Laboratories, Syracuse, N.Y. 13201, Physicians' Desk Reference 35th Edition, 1981, pp. 717 and 718). Mitomycin C and its production by fermentation is the subject of U.S. Pat. No. 3,660,578 patented May 2, 1972 claiming priority from earlier applications including an application filed in Japan on Apr. 6, 1957.

The structures of mitomycines A, B, C, and of porfiromycin were first published by J. S. Webb et al. of of Lederle Laboratories Division American Cyanamid Company, J. Am. Chem. Soc. 84, 3185–3187 (1962). One of the chemical transformations used in this structure study to relate mitomycin A and mitomycin C was the conversion of the former, 7-9$a$-dimethoxymitosane, by reaction with ammonia to the latter, 7-amino-9$a$-methoxymitosane. Displacement of the 7-methoxy group of mitomycin A has proven to be a reaction of considerable interest in the preparation of antitumor active derivatives of mitomycin C. The following articles and patents each deal inter alia with the conversion of mitomycin A to a 7-substituted amino mitomycin C derivative having antitumor activity. The object of this research was to prepare derivatives which were more active, and particularly which were less toxic than mitomycin C.

Matsui et al., J. Antibiotics, XXI, 189–198 (1968);
Konishita et al., J. Med. Chem., 14, 103–109 (1971);
Iyengar et al., J. Med. Chem., 24, 975–981 (1981);
Iyengar, Sami, Remers and Bradnet, Abstracts of Papers, 183rd Annual Meeting of the American Chemical Society, Las Vegas, Nev., March 1982, Abstract No. MEDI 72;
Iyengar et al., J. Med. Chem., 26, 16–20 (1983);
Iyengar et al., J. Med. Chem., 26, 1453–1457 (1983);
Cosulich et al., U.S. Pat. No. 3,332,944, issued Jul. 25, 1967;
Matsui et al., U.S. Pat. No. 3,420,846, issued Jan. 7, 1967;
Matsui et al., U.S. Pat. No. 3,450,705, issued Jun. 17, 1969;
Matsui et al., U.S. Pat. No. 3,514,452 issued May 26, 1970;
Nakano et al., U.S. Pat. No. 4,231,936, issued Nov. 4, 1980;
Remers, U.S. Pat. No. 4,268,676, issued May 19, 1981;
Remers, U.S. Pat. No. 4,460,599, issued Jul. 17, 1984;

Vyas et al., U.S. Pat. No. 4,487,769, issued Dec. 11, 1984.

Vyas et al., U.S. Pat. No. 4,567,256, issued Jan. 28, 1986;

Vyas et al., U.S. Pat. No. 4,579,737, issued Apr. 1, 1986;

Although there has been a considerable number of mitomycin C analogues prepared, none of the compounds of the present invention are disclosed in the references cited above or references cited therein.

SUMMARY OF THE INVENTION

The present invention is concerned with a group of mitomycin C analogs having a cyclic acetal or thioacetal substituent in the amino group at the 7-position. These compounds may be described by the general formula

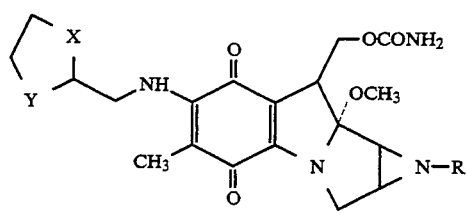

wherein R is hydrogen or methyl; and X and Y each are independently oxygen or sulfur.

The compounds of Formula I are inhibitors of experimental tumors in animals. They are employed in a manner similar to mitomycin C and, for antitumor purposes, they are administered to a mammal bearing a tumor in substantially non-toxic antitumor effective dose.

DESCRIPTION OF THE INVENTION

The present invention provides novel mitomycin C analogs having a cyclic acetal or thioacetal substituent in the amino group at the 7-position. Accordingly, there are provided novel compounds of the Formula I

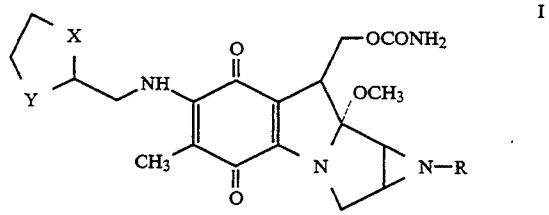

wherein
R is hydrogen or methyl; and
X and Y each are independently oxygen or sulfur.

The particularly preferred compounds of the invention are
(a) 7-[(1,3-Dioxacyclopent-2-yl)methyl]amino-9a-methoxymitosane,
(b) 7-[(1,3-Dithiacyclopent-2-yl)methyl]amino-9a-methoxymitosane and
(c) 7-[(1-Oxa-3-thiacyclopent-2-yl)methyl]amino-9a-methoxymitosane.

The compound of Formula I may be prepared by either reaction path (a) or path (b) as illustrated in Scheme 1.

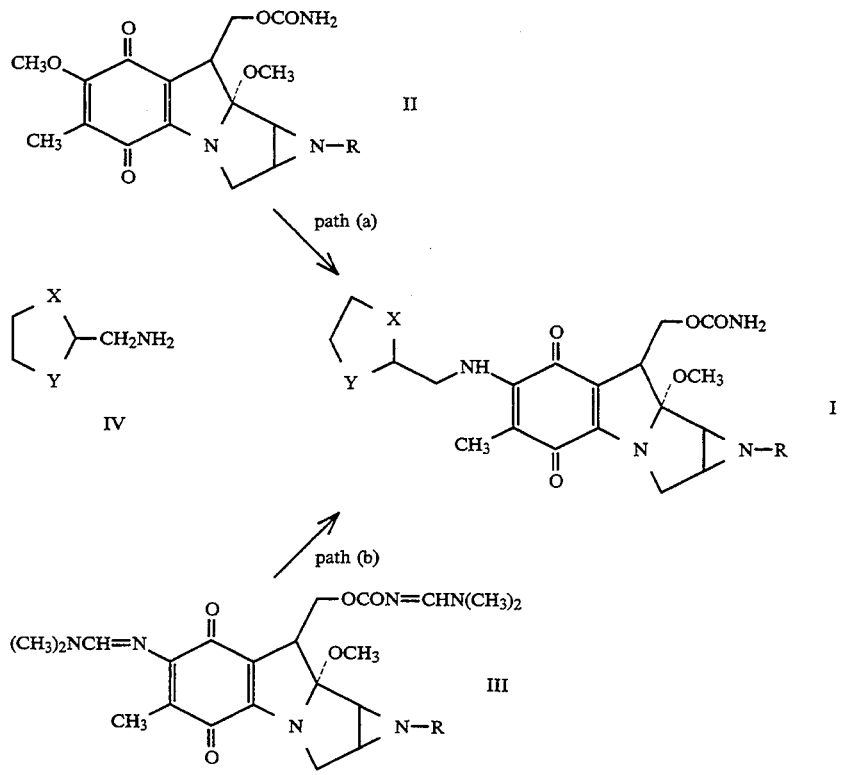

In reaction path (a), the compounds of Formula I may be prepared from the compounds of Formula II by treatment with a primary amine of the Formula IV. In a specific example described herein, the compound of Formula II wherein R is hydrogen, also commonly known as Mitomycin A, was treated with a thioacetal of Formula IV to produce the corresponding compound of Formula I wherein R is hydrogen.

Alternatively, the compounds of Formula I may be prepared from the bis-amidino compounds of Formula III and the appropriate acetals of Formula IV. The compounds of Formula III are known and may be prepared by the procedures of Vyas et al. as described in U.S. Pat. No. 4,487,769, issued Dec. 11, 1984.

The reaction conditions for the preparation of compounds of Formula I by either reaction path (a) or path (b) are not critical. The reaction may be carried out in an anhydrous organic solvent such as a lower alkanol so long as it is compatible with the reaction conditions. An excess of the primary amine reactant, on a molecular basis, is generally employed. A reaction temperature in the range of from about $-15°$ C. to about 50° C. is preferred. For convenience, we prefer to conduct the reaction in methanol at ambient temperature.

Usefulness of compounds of Formula I in antineoplastic therapeutic methods of the invention is demonstrated by the results of in vivo screening procedures wherein the compounds are administered in varying dosage amounts to mice in which a P-388 leukemic or B16 melanomic condition is induced.

Activity Against P-388 Murine Leukemia

Tables I and II contain the results of laboratory tests with $CDF_1$ mice implanted intraperitoneally with a tumor inoculum of $10^6$ ascites cells of P-388 murine leukemia and treated with various doses of either a test compound of Example 1, 2 or 3, or with mitomycin C. The compounds were administered by intraperitoneal injection. The methodology used generally followed the protocols of the National Cancer Institute [*Cancer Chemotherapy Rep.*, 3, 1–103 (1972)]. Groups of six mice were used for each dosage amount and they were treated with a single dose of the compound on the day after inoculation or they were treated with a single dose of the compound on a daily times five schedule. A group of ten saline treated control mice was included in each series of experiments. The mitomycin C treated groups were included as a positive control. A 30 day protocol was employed with the mean surival time in days being determined for each group of mice and the number of survivors at the end of the 30 day or 34 day period being noted in parenthesis. The mice were weighed before treatment and again on day five or six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. An effect in terms of % T/C equal to or greater than 125 indicates that a significant antitumor effect was achieved. The screening results in Tables I and II show that the compounds of Examples 1, 2 and 3 are useful as antitumor agents for inhibition of mammalian malignant tumors such as P-388 leukemia.

TABLE I

Inhibition of P-388 Murine Leukemia

| Material | Treatment Schedule | Dose, IP mg/kg/inj | MST Days | Effect MST % T/C | AWC, gm D. 5 | Survivors D. 5(34) |
|---|---|---|---|---|---|---|
| Mitomycin C | Day 1 | 3.2 | 28.0 | 311 | −2.2 | 6/6(1) |
| | | 1.6 | 17.0 | 189 | −1.2 | 6/6 |
| | | 0.8 | 12.5 | 139 | −0.8 | 6/6 |
| | | 0.4 | 12.0 | 133 | −0.8 | 6/6 |
| | | 0.2 | 11.5 | 128 | −0.2 | 6/6 |
| | | 0.1 | 10.0 | 111 | −0.4 | 6/6 |
| | Days 1→5 | 1.6 | 17.0 | 189 | −1.7 | 6/6 |
| | | 0.8 | 15.0 | 167 | −1.0 | 5/6 |
| | | 0.4 | 12.5 | 139 | −0.3 | 6/6 |
| | | 0.2 | 12.0 | 133 | −0.6 | 6/6 |
| | | 0.1 | 12.0 | 133 | −0.4 | 6/6 |
| | | 0.05 | 10.0 | 111 | +0.8 | 6/6 |
| Compound of Example 1 | Day 1 | 12.8 | >34.0 | >378 | −3.3 | 6/6(4) |
| | | 6.4 | 27.0 | 300 | −1.4 | 6/6(1) |
| | | 3.2 | 22.5 | 250 | −0.8 | 6/6(1) |
| | | 1.6 | 14.5 | 161 | −0.3 | 6/6 |
| | | 0.8 | 12.5 | 139 | +0.2 | 6/6 |
| | | 0.4 | 12.5 | 139 | +0.3 | 6/6 |
| | Days 1→5 | 3.2 | >34.0 | >378 | −1.5 | 6/6(3) |
| | | 1.6 | 26.5 | 294 | −1.3 | 6/6(2) |
| | | 0.8 | 16.0 | 178 | −0.5 | 6/6 |
| | | 0.4 | 13.0 | 144 | −1.0 | 6/6 |
| | | 0.2 | 12.0 | 133 | −0.5 | 6/6 |
| | | 0.1 | 11.5 | 128 | −0.2 | 6/6 |
| Compound of Example 2 | Day 1 | 12.8 | >34.0 | >378 | −2.3 | 6/6(5) |
| | | 6.4 | 12.5 | 139 | −1.3 | 6/6 |
| | | 3.2 | 15.0 | 167 | +0.1 | 6/6 |
| | | 1.6 | 12.5 | 139 | −0.1 | 6/6 |
| | | 0.8 | 12.0 | 133 | −0.8 | 6/6 |
| | | 0.4 | 12.0 | 133 | −0.4 | 6/6 |
| | Days 1→5 | 3.2 | 16.5 | 183 | −1.3 | 6/6 |
| | | 1.6 | 14.5 | 161 | −1.1 | 6/6 |
| | | 0.8 | 14.0 | 156 | −0.2 | 6/6 |
| | | 0.4 | 12.5 | 139 | −0.8 | 6/6 |
| | | 0.2 | 13.0 | 144 | +0.1 | 6/6 |
| | | 0.1 | 11.5 | 128 | +0.4 | 6/6 |
| Compound of Example 3 | Day 1 | 12.8 | >34.0 | >378 | −2.3 | 6/6(3) |
| | | 6.4 | 23.5 | 261 | −0.9 | 6/6(1) |

TABLE I-continued

| Material | Treatment Schedule | Dose, IP mg/kg/inj | MST Days | Effect MST % T/C | AWC, gm D. 5 | Survivors D. 5(34) |
|---|---|---|---|---|---|---|
| | | 3.2 | 15.5 | 172 | −0.5 | 6/6 |
| | | 1.6 | 12.5 | 139 | −0.3 | 6/6 |
| | | 0.8 | 13.0 | 144 | 0 | 6/6 |
| | | 0.4 | 11.5 | 128 | +0.4 | 6/6 |
| | Days 1→5 | 3.2 | 29.5 | 328 | −2.2 | 6/6 |
| | | 1.6 | 18.0 | 200 | −1.1 | 6/6(1) |
| | | 0.8 | 16.0 | 178 | −0.4 | 6/6 |
| | | 0.4 | 13.0 | 144 | +0.1 | 6/6 |
| | | 0.2 | 12.0 | 133 | 0 | 6/6 |
| | | 0.1 | 12.5 | 139 | +0.2 | 6/6 |
| Control | | Saline | 9.0 | — | +1.8 | 10/10 |

Tumor inoculum: $10^6$ ascites cells implanted ip.
Host: $CDF_1$ ♀ mice.
Tox: <4/6 mice alive on day 5.
Evaluation: MST = median survial time.
Effect: % T/C = (MST treated/MST control) × 100.
Criteria: % T/C ≧125 considered significant antitumor activity.
AWC: average weight change (treated-control) in grams (on day 5).

TABLE II

Inhibition of P-388 Murine Leukemia

| Material | Treatment Schedule | Dose, IP mg/kg | MST Days | Effect MST % T/C | AWC, gm D. 6 | Survivors D. 5(30) |
|---|---|---|---|---|---|---|
| Mitomycin C | Day 1 | 3.2 | 22.0 | 275 | −2.4 | 6/6 |
| | | 1.6 | 12.5 | 156 | −0.9 | 6/6 |
| | | 0.8 | 12.0 | 150 | −0.8 | 6/6 |
| | | 0.4 | 11.0 | 138 | −0.4 | 6/6 |
| | | 0.2 | 10.0 | 125 | +0.6 | 6/6 |
| | | 0.1 | 9.0 | 113 | +1.4 | 6/6 |
| Compound of Example 2 | Day 1 | 25.6 | 13.5 | 169 | −5.2 | 6/6 |
| | | 12.8 | 21.5 | 269 | −2.7 | 6/6 |
| | | 6.4 | 15.5 | 194 | −2.3 | 6/6 |
| | | 3.2 | 13.5 | 169 | −1.6 | 6/6 |
| | | 1.6 | 13.0 | 163 | −1.2 | 6/6 |
| | | 0.8 | 12.0 | 150 | −1.3 | 6/6 |
| | | 0.4 | 11.0 | 138 | +0.3 | 6/6 |
| | | 0.2 | 10.0 | 125 | −0.2 | 6/6 |
| | | 0.1 | 9.0 | 113 | +2.0 | 6/6 |
| Control | | Saline | 8.0 | — | +2.4 | 10/10 |

Tumor inoculum: $10^6$ ascites cells implanted ip.
Host: $CDF_1$ ♀ mice.
Tox: <4/6 mice alive on day 5.
Treatment: day 1 only.
Evaluation: MST = median survial time.
Effect: % T/C = (MST treated/MST control) × 100.
Criteria: % T/C ≧125 considered significant antitumor activity.
AWC: average weight change (treated-control) in grams (on day 6).

Activity Against B16 Melanoma

Table III contains results of antitumor tests using the B16 melanoma grown in mice. $BDF_1$ mice were employed and inoculated intraperitoneally with the tumor implant. Groups of ten mice were used for each dosage amount tested of either test compound of Example 1, 2, or 3, or mitomycin C, and the mean survival time for each group was determined. For each dosage level, the test animals were treated with the test compound on days 1, 5 and 9 by intraperitoneal injection. A 60 day protocol was employed with the mean survival time in days being determined for each group of mice and the number of suvivors at the end of 63 days being noted in parenthesis. Control animals inoculated in the same way as the test animals and treated with the injection vehicle and no drug exhibited a mean survival time of 20 days. The survival time relative to that of the controls (% T/C) was used as a measure of effectiveness. The minimal effective dose was defined as that dose exhibiting a % T/C value of 125. The screening results in Table III show that the compounds of Examples 1, 2 and 3 are more effective than mitomycin C with significant survivors at day 63 and, therefore, are useful as antitumor agents for inhibition of mammalian malignant tumors.

TABLE III

Inhibition of B16 Melanoma

| Material | Dose, IP mg/kg/inj | MST Days | Effect MST % T/C | AWC, gm D. 6 | Survivors D. 10(63) |
|---|---|---|---|---|---|
| Mitomycin C | 4 | 33.5 | 168 | −1.1 | 10/10 |
| | 3 | >63.0 | >315 | −1.2 | 10/10(5) |
| | 2 | 38.0 | 190 | −0.3 | 10/10(1) |
| | 1 | 37.0 | 185 | −0.5 | 10/10 |
| Compound of Example 1 | 8 | 20.0 | 100 | −1.5 | 10/10(4) |
| | 6 | >63.0 | >315 | −1.6 | 9/9(8) |
| | 4 | >63.0 | >315 | −1.7 | 10/10(9) |
| | 2 | 38.0 | 190 | −0.2 | 10/10(3) |
| Compound of Example 2 | 8 | >63.0 | >315 | −1.7 | 10/10(10) |
| | 6 | >63.0 | >315 | −1.4 | 10/10(8) |
| | 4 | >63.0 | >315 | −0.7 | 10/10(9) |
| | 2 | >63.0 | >315 | −0.5 | 10/10(6) |
| Compound of Example 3 | 8 | >63.0 | >315 | −2.5 | 10/10(8) |
| | 6 | >63.0 | >315 | −1.6 | 10/10(9) |
| | 4 | >63.0 | >315 | −1.4 | 10/10(7) |
| | 2 | >63.0 | >315 | −0.9 | 10/10(5) |
| Control | Saline | 20.0 | — | −0.6 | 10/10 |

Tumor inoculum: 0.5 ml of a 10% tumor brei, i.p.
Host: $BDF_1$ ♀ mice.
Treatment: Days 1, 5, & 9.
Evaluation: MST = median survial time.
Effect: % T/C = (MST treated/MST control) × 100.
Criteria: % T/C ≧125 considered significant antitumor activity.
AWC: average weight change (treated-control) in grams (on day 6).

In view of the antitumor activity observed in experimental animal tumors, the invention includes use of the substances of the present invention for inhibiting mammalian tumors. For this purpose, they are administered systematically to a mammal bearing a tumor in substantially non-toxic antitumor effective dose.

The compounds of the present invention are intended primarily for use by injection in much the same way and for some of the same purposes as mitomycin C. Somewhat larger or smaller doses may be employed depending upon the particular tumor sensitivity. They are readily distributed as dry pharmaceutical compositions containing diluents, buffers, stabilizers, solubilizers and ingredients contributing to pharmaceutical elegance. These compositions are then constituted with an injectable liquid medium extemporaneously just prior to use. Suitable injectable liquids include water, isotonic saline and the like.

DESCRIPTION OF SPECIFIC EMBODIMENTS

In the following examples, all temperatures are given in degrees Centigrade, and melting points are uncorrected. Proton nuclear magnetic resonance ($^1$H NMR) spectra were recorded on a Joel FX-90Q or Bruker WM360 spectrometer in pyridine-$d_5$ and the pyridine resonance at $\delta=8.57$ is used as an internal reference. Chemical shifts are reported in $\delta$ units and coupling constants in Hertz. Splitting patterns are designated as follows: s, singlet; d, doublet; t, triplet; q, quartet; m, multiplet; bs, broad singlet; dd, doublet of doublet; dt, doublet of triplet. Ultraviolet (UV) spectra were determined on a Varian-Cary 219 spectrophotometer. High resolution mass spectrum (MS) was determined with a Kratos MS-50 spectrometer and FAB ionization. All evaporations of solvents were performed under reduced pressure, and the term "ether" is diethyl ether unless otherwise indicated.

EXAMPLE 1

7-[(1,3-Dioxacyc lopent-2-yl)methyl]amino-9a-methoxymitosane

A. N-(1,3-dioxacyclopent-2-ylmethyl)amine

A mixture of 2,2-dimethoxyethylamine (10.5 g, 0.1 mole), ethylene glycol (7.45 g, 0.12 mole) in benzene was heated at reflux temperature and the water formed was collected by azeotropic distillation. After 18 hours, the reaction mixture was evaporated under reduced pressure and the residue was treated with 140 ml of 1N NaOH. The aqueous mixture was extracted with chloroform, dried and evaporated to give 10.0 g of the title compound as a yellowish liquid which was used without further pruification in the next Step.

B. 7-[(1,3-Dioxacyclopent-2-yl)methyl]amino-9a-methoxymitosane

A mixture of 7-[(dimethylamino)methylene]amino-$N^{10}$-(dimethylamino)methylene-9a-methoxymitosane (400 mg, 0.9 mmole) [prepared according to the procedure described in U.S. Pat. No. 4,487,769] and N-(1,3-dioxacyclopent-2-ylmethyl)amine (2.5 g, 24.3 mmoles) [prepared in Step A] in anhydrous methanol was stirred at room temperature for 18 hours. The resulting solution was partitioned between water and ethyl acetate. After washing with water and brine, the organic layer was dried over Na$_2$SO$_4$ and evaporated. The residue was precipitated from methylene chloride and petroleum ether to give 260 mg (44%) of the title compound; m.p.=93°–95° C.

$^1$H NMR (pyridine-$d_5$,$\delta$): 2.10 (s, 3H), 2.75 (m, 1H), 3.06 (m, 1H), 3.20 (s, 3H), 3.60 (dd, 1H), 3.90 (dd, 1H), 4.50 (d, 1H), 5.15 (t, 1H), 5.40 (dd, 1H);

UV (CH$_3$OH, $\lambda_{max}$): 219,365 nm.

High Resolution Mass Spectrum: Calc'd. for m/e: 420.1725. Found for m/e: 420.1737.

EXAMPLE 2

7-[(1,3-Dithiacyclopent-2-yl)]amino-9a-methoxymitosane

A. N-(1,3-dithiacyclopent-2-ylmethyl)amine

A mixture of 2,2-diethoxyethylamine (6.66 g, 0.05 mole), 1,2-ethanedithiol (9.42 g, 0.1 mole) and p-toluenesulfonic acid monohydrate (19.0 g, 0.1 mole) in 150 ml of benzene was heated at reflux temperature for 18 hours and the water which was thereby produced was removed azeotropically with a Dean-Stark trap. The reaction mixture was evaporated under reduced pressure and the residue treated with 50 ml of 10% NaOH. The aqueous mixture was extracted with chloroform, dried and evaporated to give 9.0 g of the title compound as an oil.

The product was dissolved in 35 ml of tetrahydrofuran and the solution was treated with a solution containing anhydrous oxalic acid (4.5 g, 0.05 mole) in 35 ml of tetrahydrofuran. The white solid was collected by filtration, washed with tetrahydrofuran and diethyl ether and dried in vacuo to give 8.0 g of the title compound as a mono-oxalate salt.

B. 7-[1,3-Dithiacyclopent-2-yl)methyl]amino-9a-methoxymitosane

A solution of N-(1,3-dithiacyclopent-2-ylmethyl)amine was prepared by adding excess triethylamine to a methanol (3 ml) solution of N-(1,3-dithiacyclopent-2-ylmethyl)-ammonium oxalate (113 mg, 0.501 mmole) [prepared in Step A]. This solution was added to a solution of mitomycin A (140 mg, 0.417 nunole) in 2 ml of methanol. After 18 hours of stirring at room temperature, the resulting solution was partitioned between water and ethyl acetate. The organic layer was washed with water and brine and dried over Na2SO4. The residue obtained after evaporation of the solvent was washed with ether to give 150 mg of the title compound; m.p.=87°–90° C.

$^1$H NMR (pyridine-$d_5$,$\delta$): 2.20 (s, 3H), 2.80 (m, 1H), 3.06 (m, 1H), 3.20 (s, 3H), 3.55 (dd, 1H), 3.90 (dd, 1H), 4.50 (d, 1H), 4.92 (t, 1H), 5.40 (dd, 1H);

UV (CH$_3$OH, $\lambda_{max}$): 220,370 mm;

Anal. Calc'd for C$_{19}$H$_{24}$N$_4$O$_5$S$_2$: C, 50.43; H, 5.35; N, 12.38. Found: C, 50.90; H, 5.70; N, 11.51.

EXAMPLE 3

7-[(1-Oxa-3-thiacyclopent-2-yl)methyl]amino-9a-methoxymitosane

A. N-(1-Oxa-3-thiacyclopent-2-ylmethyl)amine

A mixture of 2,2-diethoxyethylamine (9.32 g, 0.07 mole), 2-mercaptoethanol (7.8 g, 0.1 mole) and p-toluenesulfonic acid monohydrate (19.0 g, 0.2 mole) in 350 ml of benzene was heated at reflux temperature for 18 hours and the water which was thereby produced was removed azeotropically with a Dean-Stark trap. The reaction mixture was evaporated and the residue treated with 50 ml of 10% aqueous NaOH. The aqueous mixture was extracted with chloroform, dried and evaporated to give 6.0 g of the title compound as an oil which was further purified by vacuum distillation at 114°–123° (10–20 mmHg) to yield 2.2 g of the title compound as a colorless liquid.

B. 7-[(1-Oxa-3-thiacyclopent-2-yl)methyl]amino-9a-methoxymitosane

A mixture of mitomycin A (168 mg, 0.5 mmole) and N-(1-oxa-3-thiacyclopent-2-ylmethyl)amine (72 mg, 0.6 mmole) [prepared in Step A] in methanol (5 ml) was stirred at room temperature for 18 hours. The resulting solution was partitioned between water and ethyl acetate. The organic layer was washed with water and brine and dried over Na$_2$SO$_4$. The residue obtained after evaporation of the solvent was washed with ether to give 170 mg (74%) of the title compound; m.p.=80°-83° C.
$^1$H NMR (pyridine-d$_5$, δ): 2.10 (s, 3H), 2.70 (m, 1H), 3.10 (m, 1H), 3.20 (s, 3H), 3.60 (dd, 1H), 3.90 (dd, 1H), 4.40 (d, 1H), 5.00 (t, 1H), 5.40 (dd, 1H); UV (CH$_3$OH, λ$_{max}$): 221, 368 nm;
Anal. Calc'd for C$_{19}$H$_{24}$N$_4$O$_6$S: C, 48.71; H, 5.16; N, 11.96. Found: C, 52.27; H, 5.61; N, 12.35.
What is claimed is:
1. A compound of the formula:
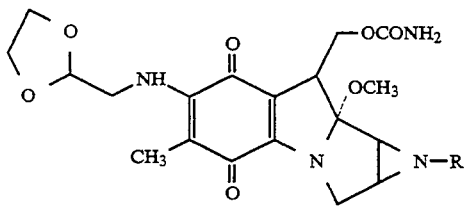
wherein R is hydrogen or methyl.
2. The compound of claim 1 which is 7-[(1,3-dioxacyclopent2-yl)methyl]amino-9a-methoxymitosane
3. A compound as defined in claim 1, wherein R is methyl.
* * * * *